United States Patent [19]
Wadman

[11] Patent Number: 5,395,355
[45] Date of Patent: Mar. 7, 1995

[54] DIAPER

[75] Inventor: Alexis A. F. Wadman, Bedfordview, South Africa

[73] Assignee: Little Feet Limited, Road Town Tortola, Virgin Islands (Br.)

[21] Appl. No.: 988,445

[22] Filed: Dec. 10, 1992

[30] Foreign Application Priority Data

Dec. 10, 1991 [ZA] South Africa ............ 91/9711

[51] Int. Cl.6 ............ A61F 13/15; A61F 13/20
[52] U.S. Cl. ............ 604/370; 604/358; 604/366; 604/367; 604/378; 604/381; 604/385.1; 604/386; 604/393; 604/397
[58] Field of Search ........... 604/358, 366, 370, 369, 604/378, 381–382, 385.1, 386–387, 392–393, 397–398, 365, 367; 428/36.1, 235–236, 245, 288, 296; 602/58

[56] References Cited

U.S. PATENT DOCUMENTS

| | | |
|---|---|---|
| 2,793,642 | 5/1957 | Andruhovici ............ 604/400 |
| 3,693,622 | 9/1972 | Jones, Sr. . |
| 3,949,130 | 4/1976 | Sabee et al. ............ 604/365 |
| 4,050,463 | 9/1977 | Schaan ............ 604/366 |
| 4,389,211 | 6/1983 | Lenaghan . |
| 4,838,886 | 6/1989 | Kent ............ 604/393 |
| 4,900,318 | 2/1990 | Toth ............ 604/385.1 |
| 5,073,316 | 12/1991 | Bizen et al. . |

FOREIGN PATENT DOCUMENTS

| | | |
|---|---|---|
| 481322A | 4/1992 | European Pat. Off. . |
| 546821 | 6/1993 | European Pat. Off. ............ 604/365 |

Primary Examiner—Randall L. Green
Assistant Examiner—P. Zuttarelli
Attorney, Agent, or Firm—Jones, Day, Reavis & Pogue

[57] ABSTRACT

A disposable diaper comprises an absorbent non-woven polypropylene material shaped to be located in use over the crotch between the legs of the user to substantially cover the front and rear of the lower torso, the outer surface of the material being treated to form a smooth surface of bonded material which will inhibit the passage of liquid.

15 Claims, 3 Drawing Sheets

DIAPER

FIELD OF THE INVENTION

This invention relates to a diaper, such as that worn by babies or by incontinent person in general.

BACKGROUND TO THE INVENTION

There are generally two types of diapers, the one being of a cloth material and being re-washable and re-usable, and theother being of an absorbent material and intended to be disposed of after use.

One of the problems with disposable diapers is sizing them for a proper fit, and another problem lies in the actual disposal of the diaper. Most disposable diapers have non-biodegradable material in them, and the disposal of large quantities of these diapers can be an environmental problem, and also a health problem in certain cases.

OBJECT OF THE INVENTION

It is an object of this invention to provide a disposable diaper which can alleviate some of the difficulties mentioned above.

SUMMARY OF THE INVENTION

In accordance with this invention there is provided a diaper comprising an absorbent non-woven material shaped to be located in use over the crotch between the legs of the user to substantially cover the front and rear of the lower torso, the outer surface of the material being treated to form a smooth surface of bonded material which will inhibit the passage of liquid.

Further features of the invention provide for the material to have memory enabling it to substantially retain its form after shaping. The material may include polypropylene, and there is provided for the treatment to be a heat treatment, or alternatively a pressure treatment, or a combination of both.

There is further provided for the material to be shaped over a former representing a lower torso, and for the treatment to form the material in this shape, leaving the material resiliently flexible for location in use.

There is further provided for there to be an inner lining fitted to the inner surface of the material, and preferably the lining is bonded to the material along the edges thereof, by a heat or pressure treatment.

A liquid absorbent substance, such as a gel or crystals, may be included in an absorbent pad along the centre line of the material where liquid is expected to pass.

The invention extends to include, when desired, an outer waterproof covering with front and back sections, of substantially the same shape as the diaper material, and being locatable over the diaper with front and back sides securable relative to each other to secure the outer waterproof cover in position.

There is provided for the sides of the waterproof covering to have tabs which overlap at the waist level in operative orientation, and by which the covering can be secured over the diaper in use.

Still further, there is provided for one tab of each securable pair of tabs to be securable to the diaper material through an opening in the other tab. The openings may be spaced apart along the waistline for adjustable securement.

Alternatively, when no waterproof covering is to be used, fixing means are located to secure opposing front and back corners of the diaper.

The invention extends to a method of manufacturing a diaper, including forming an absorbent non-woven material around a former representing a torso, and treating the outer surface of the material to cause the outer surface to form a smooth surface of bonded material which will inhibit the passage of liquid.

Preferably the treatment also causes the material to take the general shape of the former.

There is provided for the material to have a memory enabling it to substantially retain its form after shaping. The material may include polypropylene, and the treatment may be a heat treatment.

There is also provided for the step of fitting an inner lining to the material, by bonding it along the edges of the material, preferably by heat treatment, but alternatively by a pressure treatment, or a combination of both.

BRIEF DESCRIPTION OF THE DRAWINGS

A preferred embodiment of the invention is described below by way of example only, and with reference to the accompanying drawings, in which.

DETAILED DESCRIPTION OF THE DRAWINGS

Figure 1:
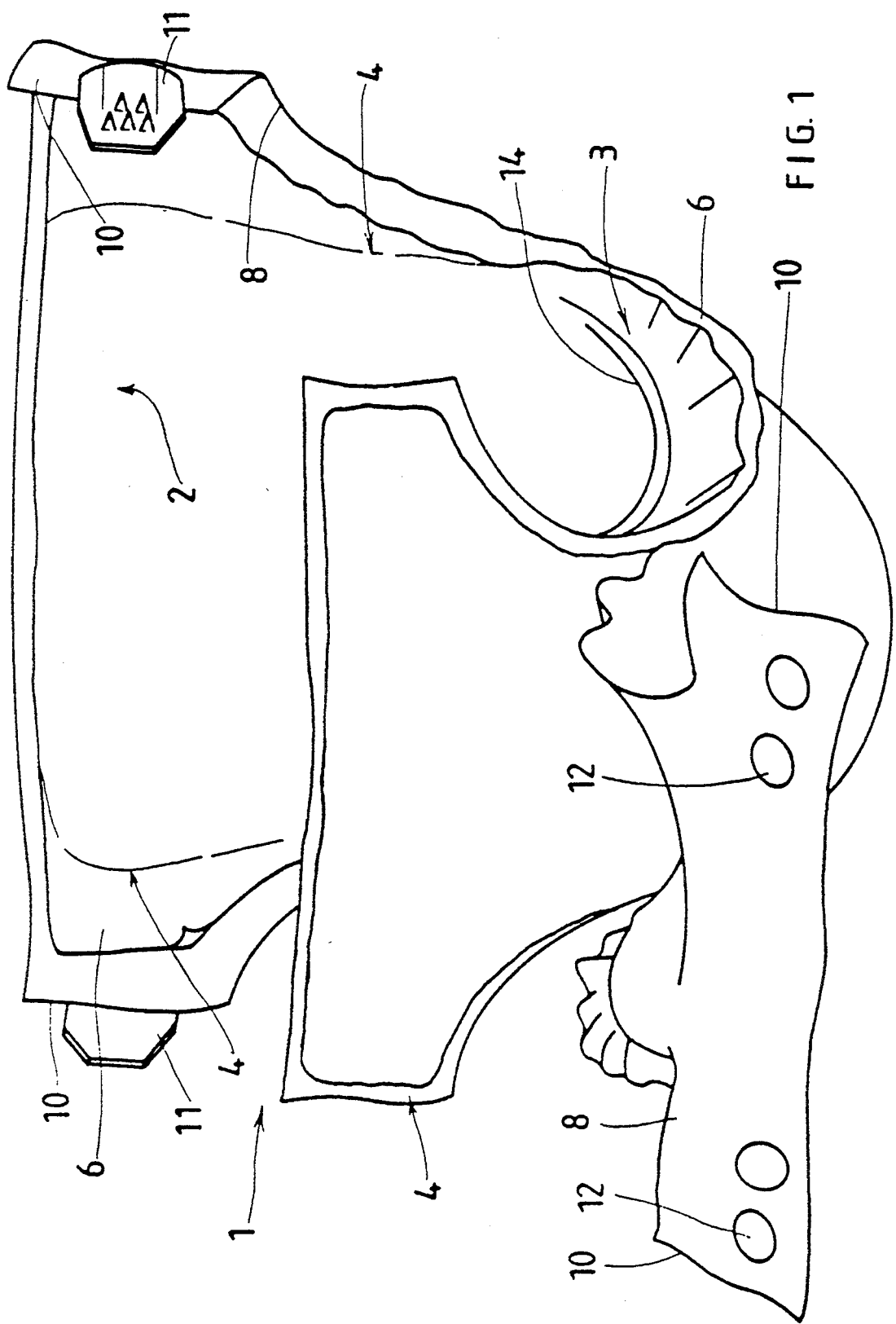
FIG. 1 is a front isometric view illustrating a diaper according to the invention.
Figure 2:
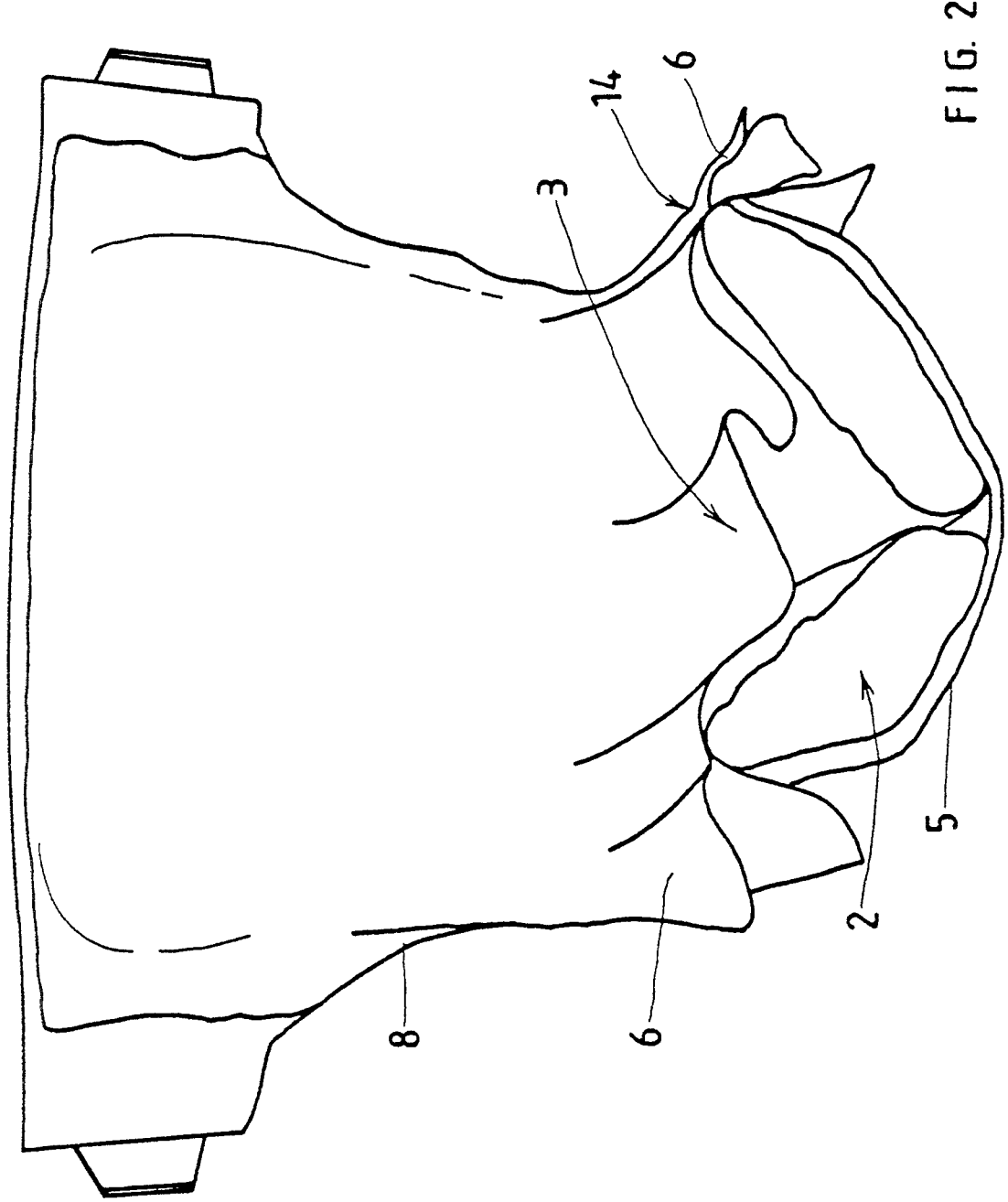
FIG. 2 is a similar view as that of FIG. 1, but showing the diaper in section; and, FIG. 3 shows the diaper in use fitted to a user.

Referring to FIGS. 1 and 2, a diaper (1) comprises a non-woven material (2) including a proportion of polypropylene. The woven material is shaped around a former of a torso, to cover the torso efficiently in the manner of a diaper. The material is supplied in a matting which is cut to shape and located over the former.

On the inner side of the diaper material (2) is an inner lining (3) which is provided for comfort and which allows passage of liquid.

The outer surface of the material over the former is heat treated to cause a seam (4) around the edges to define the shape of a diaper, and to bond the outer surface of the material to form a smooth surface (5) which inhibits the passage of liquid.

Beyond the edges (4), an untreated portion of the material (6) is left as excess facing which extends beyond the seam (4) around the diaper. The lining material is bonded to the diaper material (2) along the seam line (4), and this may be done at the same time as the heat treatment over the former is performed.

Around the bonded outer surface (5) of the material, is a separate waterproof covering in the form of a pair of waterproof pants (8). The waterproof pants (8), when used, are in the same general shape as the diaper material, and are separated at the sides. The sides are provided with pairs of tabs (10) which meet in use over the torso and by which the waistband of the pants can be secured together.

Alternatively, when no waterproof covering is to be used, fixing means are located to secure opposing front and back corners of the diaper.

Figure 3:
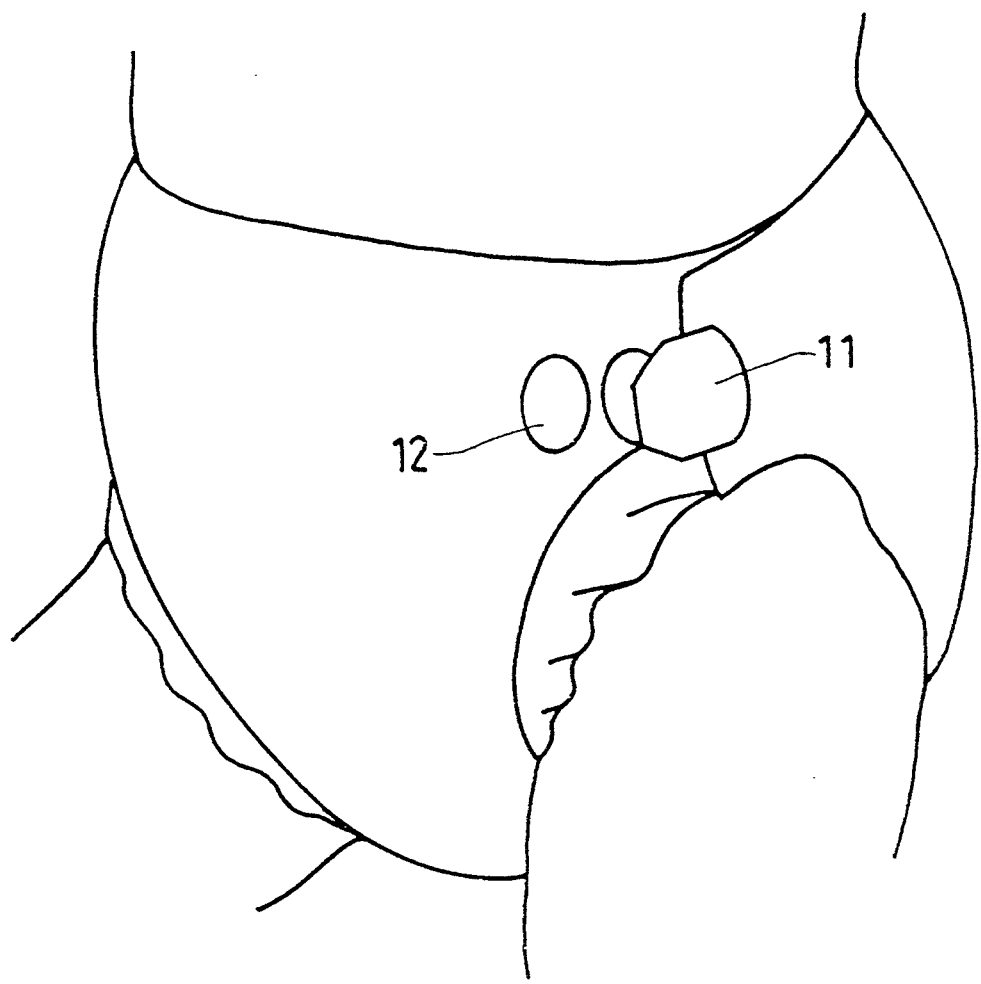

This embodiment provides for the tabs to be secured by means of a "Velcro" type fitting (11) fitted to one tab of each pair. This tab locates through and over an opening (12) in the other tab of the pair, to be exposed to the inner surface of the diaper when in operative orientation (FIG. 3). Alternatively other forms of securement may be used.

A liquid absorbent gel or crystal in a pad may be located between the material and the lining (3) over the crotch area, if desired.

In use, the formed diaper comprising the material, bonded on the outside, and with the lining on the inside, is located around a baby. The outer waterproof, if used, is then located over the diaper if maximum sealing is required. The waterproof and diaper can also be fitted at the same time. The outer waterproof is then secured in position by the location of the tabs (11) over the openings (12), to become attached to the outer surface of the diaper material through the openings. A number of openings (12) may be provided spaced apart along the waistband to allow for variable adjustment of the waist size.

The seam line (4), being formed by a heat treatment over the former, creates a ridge (14) on each side of the crotch, which projects inwardly to fit snugly between the crease of each leg and the crotch. Since the excess facing material (6), which extends from the seam line, is not bonded in any way and is still soft, this forms a comfortable sealing surface between the legs. The waterproof pants extend over this area, and has its crotch edging tucked in behind the seam and ridge (14), to form the seal around the crotch area which is necessary to cause the liquid to be absorbed effectively by the diaper material, and limit escape of liquid from the diaper.

If no waterproof is used, the fitting and use follows that described above, save that securing tabs or adhesive tape or the like, is used to join the front and back corners at the waist.

It is considered that the invention provides an effective diaper which requires no special sewing or other sealing means around the edges, and which allows for the absorbent material to be disposed of, and an outer waterproof material to be re-used. This reduces the environmental hazard of the diaper if the material that is disposed of is bio-degradable, and also reduces the overall cost of the diaper since the waterproofing element is re-usable.

What is claimed is:

1. A diaper having an inner and an outer surface, said diaper comprising a unitary absorbent non-woven material shaped to be located in use over a crotch between legs of a user of the diaper to substantially cover front and rear portions of a lower torso of said user, the outer surface of the material being treated to form a smooth surface of unlaminated bonded material inhibiting passage of liquid.

2. A diaper as claimed in claim 1 in which the material is subjected to a heat treatment.

3. A diaper as claimed in claim 1 in which the material is resiliently flexible enabling fitting engagement of the diaper on the torso of the user.

4. A diaper as claimed in claim 1 in which a liquid absorbent substance is included along the center line of the material where liquid is expected to pass.

5. A diaper as claimed in claim 1 in which the material is subject to a pressure treatment.

6. A diaper as claimed in claim 1 in which the material is subjected to a combination of a heat treatment and a pressure treatment.

7. A diaper as claimed in claim 1 in which is included an outer waterproof covering with front and back sections, of substantially the same shape as the diaper material, which is locatable over the diaper with front and back sides securable relative to each other to secure the diaper and outer waterproof cover in position.

8. A diaper as claimed in claim 7 in which the waterproof covering, has tabs which overlap at a user's waist level in operative orientation, and by which the covering can be secured over the diaper in use.

9. A diaper as claimed in claim 1 in which the material has a memory enabling it to substantially retain its shape after forming.

10. A diaper as claimed in claim 9 wherein said material comprises polypropylene.

11. A diaper having an inner and an outer surface, said diaper comprising a unitary absorbent non-woven material shaped to be located in use over a crotch between legs of a user of the diaper to substantially cover front and rear portions of a lower torso of said user, the outer surface of the material being treated to form a smooth unlaminated surface of bonded material inhibiting passage of liquid and said diaper having an inner lining fitted to the inner surface of the material.

12. A diaper as claimed in claim 11 in which the lining is bonded to the material along inside edges thereof.

13. A diaper as claimed in claim 12 in which said lining is bonded to the material along the inside edges thereof, by a treatment selected from the group consisting of heat treatment, pressure treatment and a combination of heat and pressure treatment.

14. A diaper having an inner and an outer surface, said diaper comprising a unitary an absorbent non-woven material shaped to be located in use over a crotch between legs of a user of the diaper to substantially cover front and rear portions of a lower torso of said user, the outer surface of the material being treated to form a smooth surface of unlaminated bonded material inhibiting passage of liquid, an outer waterproof covering with front and back sections, of substantially the same shape as the diaper material, which is locatable over the diaper with front and back sides securable relative to each other to secure the diaper and outer waterproof cover in position, said waterproof covering having tabs which overlap at the user's waist level in operative orientation for securing the covering over the diaper in use, each tab being securable to the diaper material through an opening in another tab.

15. A diaper as claimed in claim 14 in which a plurality of openings are formed therein at the user's waist level, said openings being spaced apart enabling adjustable securement of said tabs.

* * * * *